United States Patent [19]

Chiulli

[11] 4,282,972
[45] Aug. 11, 1981

[54] PAN FOR ANGIOGRAPHIC CATHETERS

[76] Inventor: Robert D. Chiulli, 71 Cherry St., Somerville, Mass. 02144

[21] Appl. No.: 121,694

[22] Filed: Feb. 15, 1980

[51] Int. Cl.³ .............. B65D 85/04; B65D 1/36; B65D 3/28; B65D 5/48
[52] U.S. Cl. .................... 206/303; 206/364; 206/561; 220/20; 134/84
[58] Field of Search ............ 206/565, 561, 303, 314, 206/387, 389, 364; 220/20, 22; 134/84

[56] References Cited

U.S. PATENT DOCUMENTS

| 718,114 | 1/1903 | Finney | 206/314 |
|---|---|---|---|
| 874,562 | 12/1907 | Bliss | 134/84 |
| 979,858 | 12/1910 | Hotze | 206/561 |
| 1,356,362 | 10/1920 | Hensal | 134/84 |
| 1,752,137 | 3/1930 | Ahearn | 134/84 |
| 2,969,146 | 1/1961 | Metz | 206/364 |
| 3,216,565 | 11/1965 | Davis et al. | 206/303 |
| 3,561,595 | 2/1971 | Weggeland | 206/387 |

Primary Examiner—William T. Dixson, Jr.
Attorney, Agent, or Firm—Scott R. Foster

[57] ABSTRACT

A pan for angiographic catheters and catheter guide wires, the pan including a rectangular planar bottom portion, four walls upstanding from the ends thereof to form a basin adapted to retain a liquid, and divider structure upstanding from the bottom portion and dividing the basin into a plurality of compartments, an opposed pair of the walls being inclined inwardly, the divider structure extending normal to the inclined pair of walls, the divider structure having a first portion inclined in a first direction and a second portion inclined in a second direction.

10 Claims, 3 Drawing Figures

PAN FOR ANGIOGRAPHIC CATHETERS

BACKGROUND OF THE INVENTION

1. Field of the Invention

The invention relates to receptacles for surgical instruments and is directed more particularly to a pan adapted to receive and retain angiographic catheters and catheter guide wires.

2. Description of the Prior Art

Known radiographic procedures facilitate study and non-surgical therapy of vascular, ductal, vesical and cyst-like structures of normal or pathologic origin. Such studies encompass arteriography, venography, transluminal angioplasty, and percutaneous drainage procedures.

Percutaneous procedures essentially involve the use of guide wires and catheters. There are a multiplicity of types, sizes and configurations of guide wires and catheters unique to the intended use or the anatomy to be examined or manipulated. However, the basic function of all guide wires and of all catheters remains the same.

The catheter is a tube configured for its intended use and provided with a fitting which permits connection of the catheter to a syringe or injector for the introduction or withdrawal of fluids. The guide wire is a wire of varying flexibility and end shape which can be introduced through a needle bore into an artery, vein, or tubular structure to be examined, and advanced along and within same. Its function is to maintain access and provide stability and guidance for the catheter.

In a known procedure, a needle puncture is made through the skin, into an artery, vein or viscus. A guide wire is advanced through the needle bore into and within the vessel. The needle is then withdrawn, leaving the wire in position defining a pathway from the skin to a selected structure. A catheter is advanced over the external portion of the wire, through the puncture, and into the vessel, the catheter being guided and stabilized by the wire. When the catheter is appropriately positioned, the guide wire is withdrawn, leaving the catheter in position to effect examination or therapy. Radiographic constrast media or medication may be injected, or fluids sampled, or structures drained. Should repositioning, replacement, or exchange of catheters be required, an appropriate guide wire is reintroduced through the positioned catheter, which can then be repositioned, or withdrawn, over the wire. New catheters may be introduced over the wire as many times as is necessary to complete the study.

Catheters and guide wires are generally prepackaged, sterile and usually disposable items. Repetitive use and exchange of the catheters and guide wires are frequently made during a given procedure to accomplish the objectives of the study. It is common to use and reuse several different guide wires and catheters in a given procedure.

During such procedures, it is necessary that guide wires and catheters set aside for later use be maintained in a sterile atmosphere, be readily accessible to the operator, be completely immersed in a wash solution, be completely immersed in an anticoagulant solution (for some procedures), and be segregated so that they may be readily identified and used without becoming intertwined with other stored wires and/or catheters.

It has been customary to use as a storage or holding mechanism a basin or pan filled with a physiologic solution to which has been added an anticoagulant. The wires and catheters are coiled when removed from the patient and the coil immersed in the solution, thereby maintaining a sterile, anticoagulative wash atmosphere. However, since the basin or pan is without compartmentalization, the wires and catheters cannot be stored separately in the pan and tend to become entangled with each other, making it difficult and time consuming to identify and separate one from the other. Furthermore, the usual configuration of basins and pans includes vertical or outwardly sloping walls from bottom to top. Such configuration, in conjunction with the expansile nature of the coiled wires and catheters renders the usual container unsatisfactory. The tendency of the guide wires and catheters to uncoil and spring upwards makes it difficult to retain them and particularly to insure that they remain submerged in the solution.

SUMMARY OF THE INVENTION

An object of the present invention is to provide a pan for angiographic catheters and catheter guide wires, the pan being adapted to retain such implements each in a separate compartment to prevent entanglement of the implements.

A further object of the invention is to provide such a pan having facility for retaining an appropriate solution and for accommodating a guide wire or catheter in a coiled condition, retaining such implement below the level of solution.

With the above and other objects in view, as will hereinafter appear, a feature of the present invention is the provision of a pan for angiographic catheters and catheter guide wires, the pan comprising a rectangular planar bottom portion, a first pair of walls comprising a first wall upstanding from a first end of the bottom portion and a parallel second wall upstanding from a second end of the bottom portion, a second pair of walls comprising a third wall upstanding from a third end of the bottom portion and a parallel fourth wall upstanding from a fourth end of the bottom portion, the first pair of walls being inclined from the bottom portion inwardly toward each other, the walls and the bottom portion forming a basin adapted to retain a liquid, and divider means upstanding from the bottom portion and extending normal to the first pair of walls, the divider means dividing the basin into a plurality of compartments, the divider means having a first barrier portion inclined toward a first of the compartments and a second barrier portion inclined toward a second of the compartments.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention from which its novel features and advantages will be apparent.

In the drawings.

DESCRIPTION OF THE PREFERRED EMBODIMENTS

Figure 1:
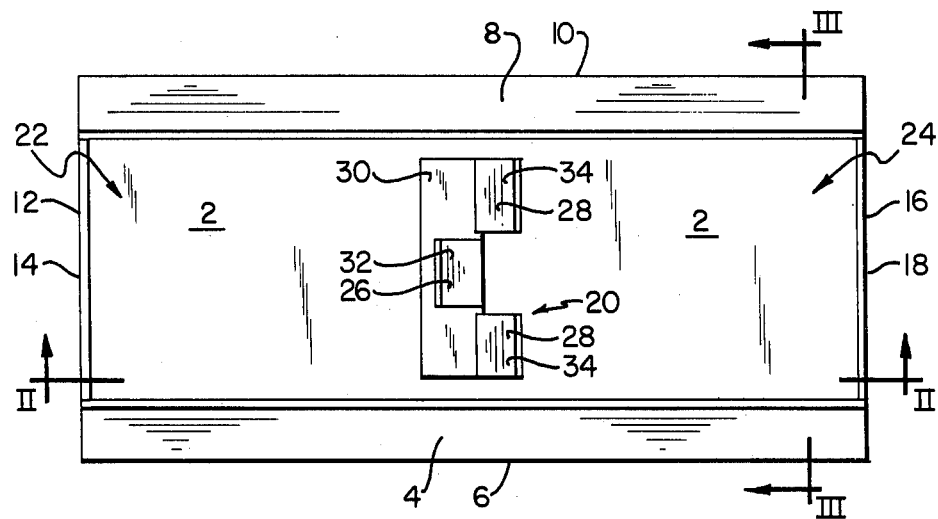
FIG. 1 is a plan view of a pan for angiographic catheter guide wires and catheters, illustrative of an embodiment of the invention.
Figure 2:
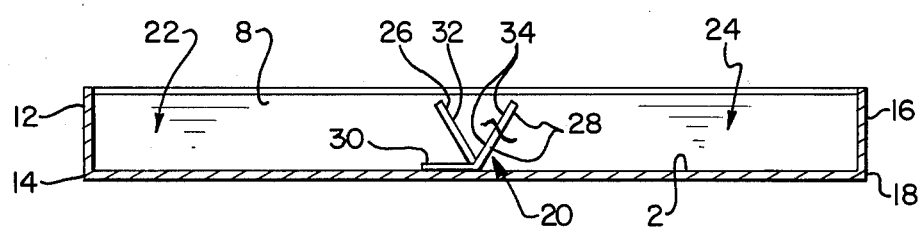
FIG. 2 is a sectional view, taken along line II—II of FIG. 1.
Figure 3:
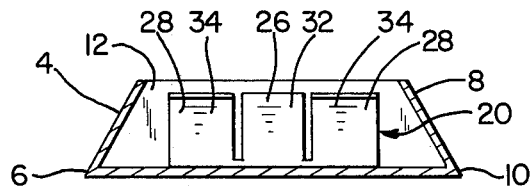
FIG. 3 is a sectional view taken along line III—III of FIG. 1.

Referring to the drawings, it will be seen that the illustrative embodiment comprises a pan including a rectangular planar bottom portion 2. Fixed to the bottom portion 2 is a first pair of walls including a first wall 4 upstanding from a first end 6 of the bottom portion and a second wall 8 upstanding from a parallel second end 10 of said bottom portion. Also fixed to the bottom portion 2 is a second pair of walls including a third wall 12 upstanding from a third end 14 of the bottom portion, and a fourth wall 16 upstanding from a parallel fourth end 18 of the bottom portion. The first pair of walls 4, 8 are inclined from the bottom portion 2 inwardly toward each other, as may be seen in FIG. 3. The walls, 4, 8, 12, 16 and the bottom portion 2 form a basin adapted to retain a liquid, such as an appropriate saline solution.

The pan further includes a divider means 20 upstanding from the bottom portion and extending normal to the first pair of walls 4, 8. The divider means 20 divide the basin into a plurality of compartments 22, 24. The divider means 20 is provided with a first barrier portion 26 inclined toward the first of the compartments 22 and a second barrier portion 28 inclined toward the second of the compartments 24.

If the pan is metal, the divider means 20 is preferably of metal and may include a base flange member 30 fixed to an upper surface of the bottom portion 2, the first and second barrier portions 26, 28 comprising extensions of the base flange member bent upwardly as shown. Preferably the barrier portions 26, 28 comprise alternate flange portions, the first barrier portion 26 comprising a central flange portion 32, and the second barrier portion 28 comprising a pair of flange portions 34 on either side of the central flange portion 32.

The divider means 20 is disposed so as to provide for equal sized compartments 22, 24, the divider means being substantially normal to, but removed from, the walls 4, 8.

In lieu of metal, the illustrative pan may be of molded plastic, in which case the device may be of one-piece construction, the walls, bottom portion and divider means being molded as a unitary element.

The divider means 20 may comprise upstanding studs, rather than the barrier portions illustrated.

In use, the pan is placed conveniently for the operation at hand with an appropriate saline solution therein. Catheters and catheter wires are placed in the pan in a coiled condition. The tendency of the coils to expand causes the coiled members to bear against the inwardly-extending walls which urge the coiled members toward the bottom of the pan and beneath the surface of the solution. To the extent possible, depending upon the number of catheters and wires needed and the number of compartments available in the pan, the various coiled members are retained in separate compartments to prevent entanglement of members. When it is desired to lift a member from the pan, an operator need only grasp the coiled instrument along any arcuate portion not contiguous with the pan walls, and lift the coiled member from the compartment. The walls 12, 16 being generally normal to the bottom portion 2 of the pan facilitate easy removal of the coiled members. When it is desired to return the coiled member to the pan, the member is placed in its compartment, beneath the free edges of the inclined walls 4, 8 and the divider means 20, the obliqueness of the inclined walls and divider means urging the coiled member toward the bottom of the pan and beneath the surface of the solution therein.

It is to be understood that the present invention is by no means limited to the particular construction herein disclosed and/or shown in the drawings, but also comprises any modifications or equivalents within the scope of the disclosure.

For example, though a pan with two compartments is illustrated, it is contemplated that pans having more than two compartments would be most helpful and appropriate for various operative procedures.

Having thus described my invention what I claim as new and desire to secure by Letters Patent of the United States is:

1. A pan for angiographic catheters and catheter guide wires, the pan comprising a rectangular planar bottom portion, a first pair of walls comprising a first wall upstanding from a first end of said bottom portion and a second wall upstanding from a parallel second end of said bottom portion, a second pair of walls comprising a third wall upstanding from a third end of said bottom portion and a fourth wall upstanding from a parallel fourth end of said bottom portion, said first pair of walls being inclined from said bottom portion inwardly toward each other, said walls and said bottom portion forming a basin adapted to retain a liquid, and divider means upstanding from said bottom portion and extending generally normal to said first pair of walls, said divider means dividing said basin into a plurality of compartments, said divider means having a first barrier portion extending toward a first of said compartments and a second barrier portion extending toward a second of said compartments.

2. The invention in accordance with claim 1 in which said first and second barrier portions comprise alternate portions of said divider means.

3. The invention in accordance with claim 2 in which said first barrier portion comprises a pair of flange members and said second barrier portion comprises a flange member disposed between said pair of flange members.

4. The invention in accordance with claim 3 in which said pan is of metal and said divider means is of metal and includes a base flange portion fixed to an upper surface of said bottom portion, said flange members comprising extensions of said base flange portion.

5. The invention in accordance with claim 1 in which said pan is of plastic and comprises a molded one-piece unit.

6. The invention in accordance to claim 1 in which the longer of said pairs of walls are inclined inwardly.

7. The invention in accordance with claim 6 in which the shorter of said pairs of walls are disposed normal to said bottom portion.

8. The invention in accordance with claim 7 in which said pan is of metal and said divider means is of metal and includes a base flange portion fixed to an upper surface of said bottom portion, said flange members comprising extensions of said base flange portion.

9. The invention in accordance with claim 7 in which said pan is of plastic and comprises a molded one-piece unit.

10. The invention in accordance with claim 1 in which said divider means is removed from said walls.

* * * * *